(12) United States Patent
McKay et al.

(10) Patent No.: US 8,012,139 B2
(45) Date of Patent: Sep. 6, 2011

(54) DEVICES AND METHODS FOR DELIVERING MEDICAL AGENTS

(75) Inventors: William F. McKay, Memphis, TN (US); Susan J. Drapeau, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/859,391

(22) Filed: Aug. 19, 2010

(65) Prior Publication Data

US 2010/0312173 A1 Dec. 9, 2010

Related U.S. Application Data

(63) Continuation of application No. 11/118,125, filed on Apr. 29, 2005.

(51) Int. Cl.
*A61M 1/00* (2006.01)
*A61M 31/00* (2006.01)
*A61M 5/00* (2006.01)

(52) U.S. Cl. .......... 604/506; 604/28; 604/173; 604/191; 604/239

(58) Field of Classification Search .......... 604/173, 604/191, 239, 28, 506, 522
See application file for complete search history.

(56) References Cited

U.S. PATENT DOCUMENTS

| | | |
|---|---|---|
| 4,013,080 A | 3/1977 | Froning |
| 4,014,333 A | 3/1977 | McIntyre |
| 4,338,925 A | 7/1982 | Miller |
| 5,219,358 A | 6/1993 | Bendel et al. |
| 5,354,279 A | 10/1994 | Hofling |
| 5,415,182 A | 5/1995 | Chin et al. |
| 5,611,809 A | 3/1997 | Marshall et al. |
| 5,628,734 A | 5/1997 | Hatfalvi |
| 5,824,087 A | 10/1998 | Aspden et al. |
| 5,968,008 A | 10/1999 | Grams |
| 6,048,346 A | 4/2000 | Reiley et al. |
| 6,077,251 A | 6/2000 | Ting et al. |
| 6,126,682 A | 10/2000 | Sharkey et al. |
| 6,217,554 B1 | 4/2001 | Green |
| 6,241,710 B1 | 6/2001 | VanTassel et al. |
| 6,241,734 B1 | 6/2001 | Scribner et al. |
| 6,245,046 B1 | 6/2001 | Sibbitt |
| 6,261,311 B1 | 7/2001 | Sharkey et al. |
| 6,300,127 B1 | 10/2001 | Hair et al. |
| 6,425,887 B1 | 7/2002 | McGuckin et al. |
| 6,432,092 B2 | 8/2002 | Miller |
| 6,517,568 B1 | 2/2003 | Sharkey et al. |
| 6,592,559 B1 | 7/2003 | Pakter et al. |
| 6,840,921 B1 | 1/2005 | Haider et al. |
| 7,094,222 B1 | 8/2006 | Siekas et al. |
| 2001/0016703 A1 | 8/2001 | Wironen et al. |
| 2001/0023349 A1 | 9/2001 | VanTassel et al. |
| 2002/0058947 A1 | 5/2002 | Hochschuler et al. |
| 2002/0099384 A1 | 7/2002 | Scribner et al. |
| 2002/0111603 A1 | 8/2002 | Cheikh |
| 2002/0151867 A1 | 10/2002 | McGuckin, Jr. et al. |

(Continued)

FOREIGN PATENT DOCUMENTS

GB 3555 2/1910

(Continued)

*Primary Examiner* — Theodore J Stigell
*Assistant Examiner* — Imani Hayman

(57) ABSTRACT

Described are novel methods for delivering a medical agent to a plurality of locations within a patient tissue volume such as the interior space of a spinal disc, and also for removing material therefrom during medical agent delivery to enhance the delivery. Also described are medical delivery devices such as needle assemblies configured to facilitate the regional delivery of medical agents to patient tissue.

10 Claims, 16 Drawing Sheets

U.S. PATENT DOCUMENTS

2004/0092894 A1  5/2004  Hung et al.
2004/0215130 A1  10/2004  Rioux et al.
2004/0220536 A1  11/2004  VanTassel et al.

FOREIGN PATENT DOCUMENTS

| WO | 0033909 A1 | 6/2000 |
| WO | 0234113 A2 | 5/2002 |
| WO | 2004030726 A1 | 4/2004 |
| WO | 2004075954 A2 | 9/2004 |

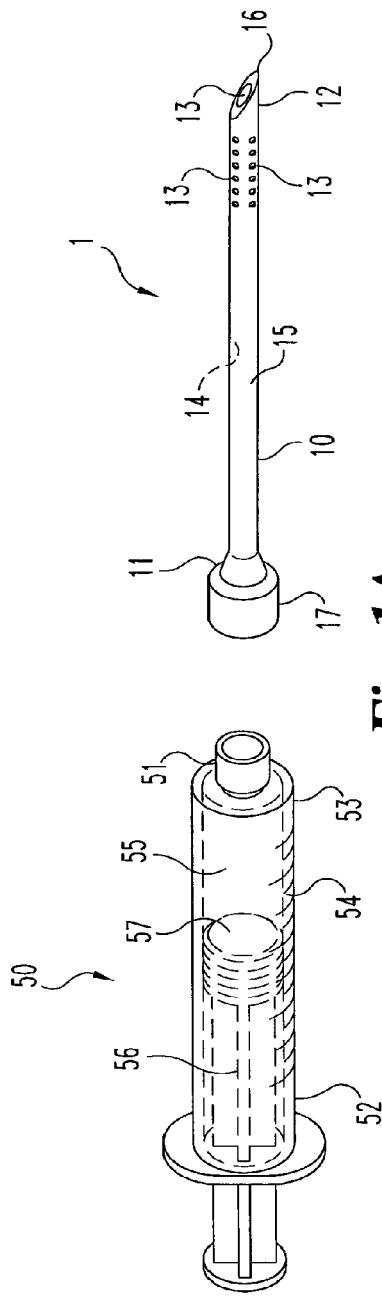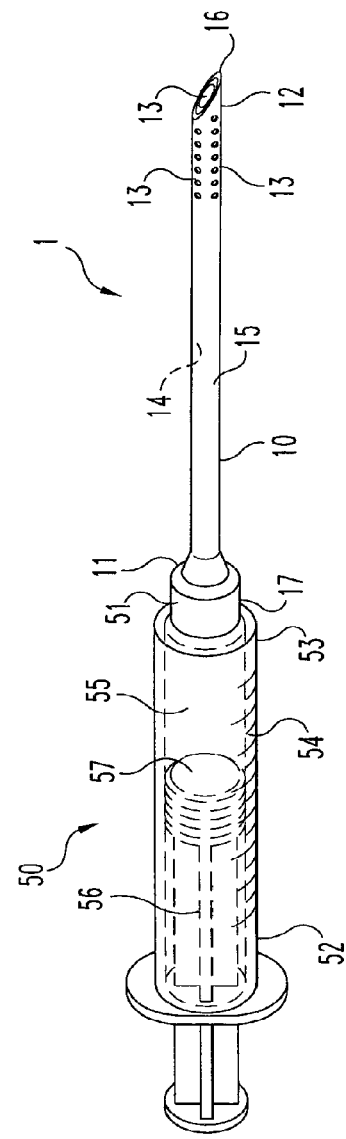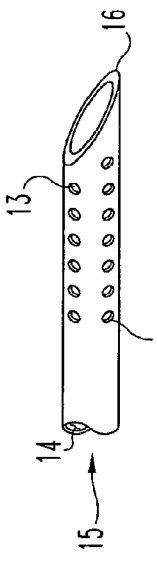

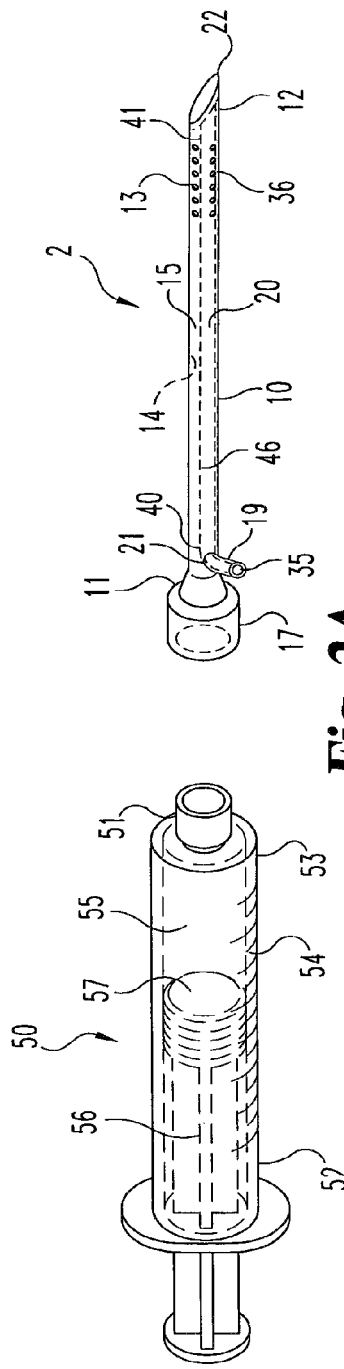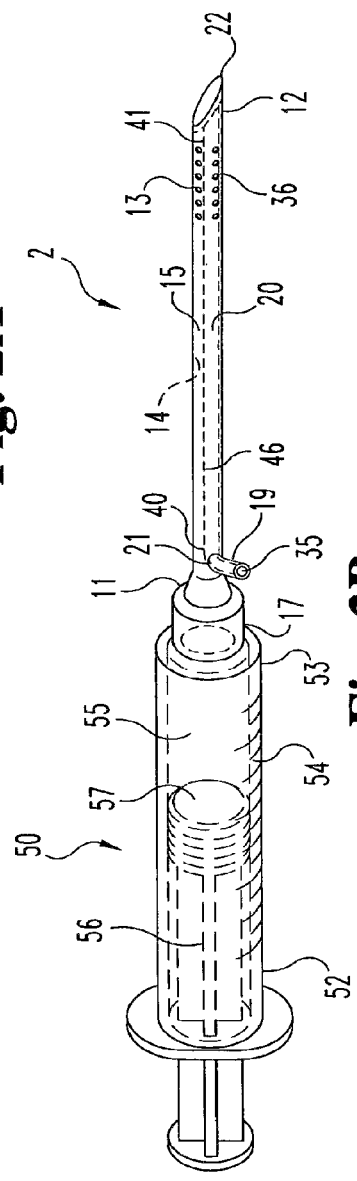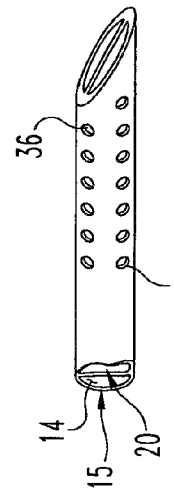
Fig. 2A
Fig. 2B
Fig. 2C

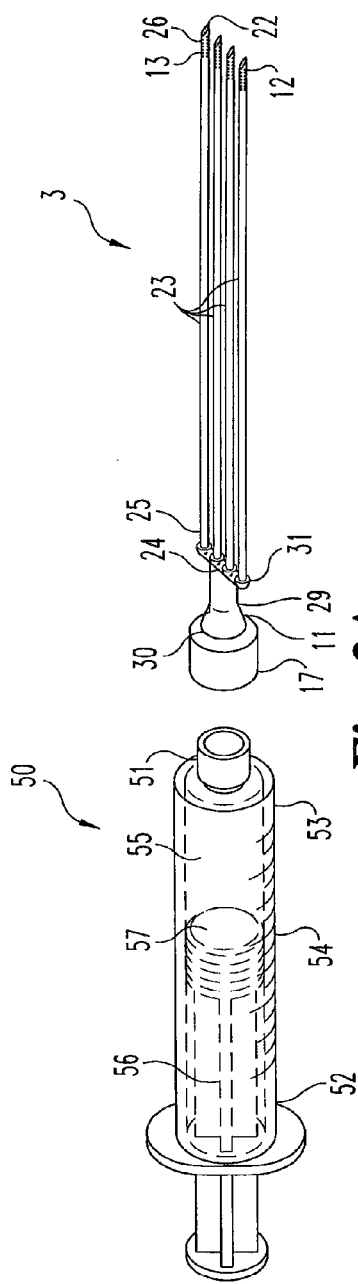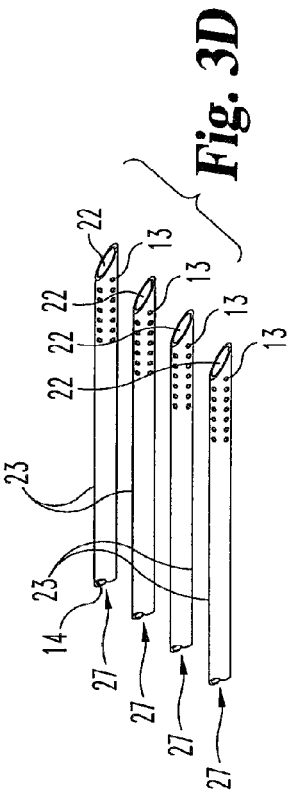
Fig. 3A  Fig. 3B  Fig. 3D

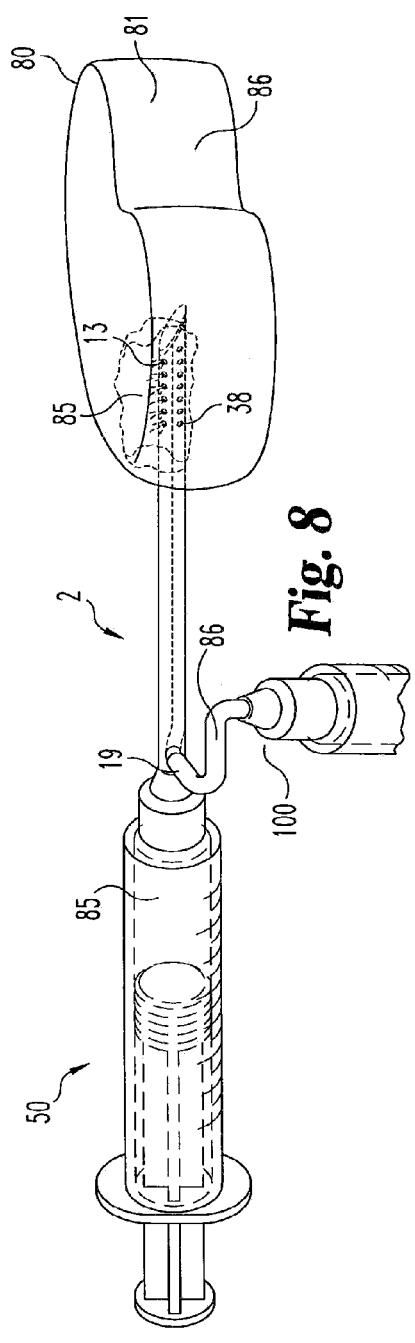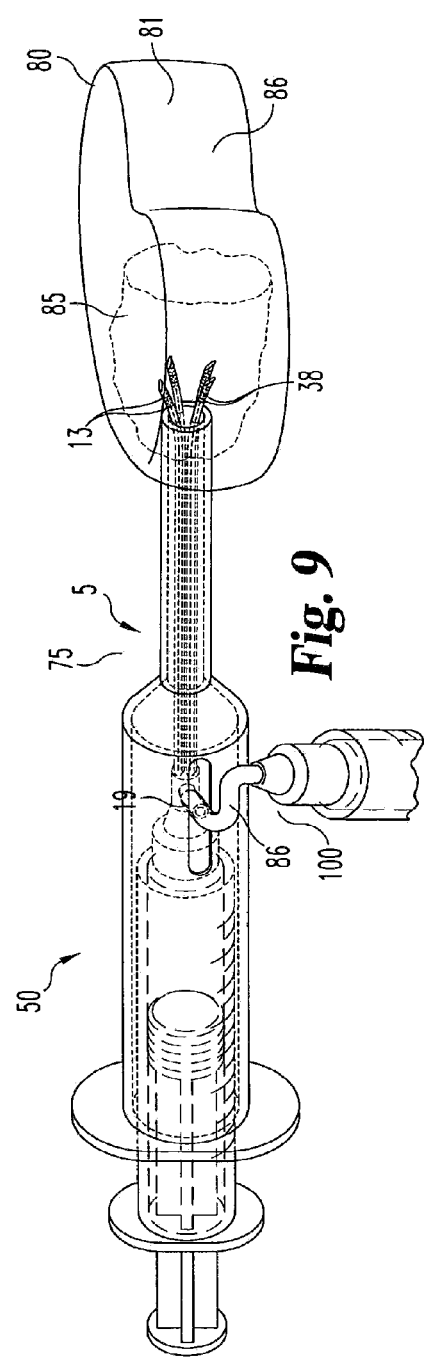

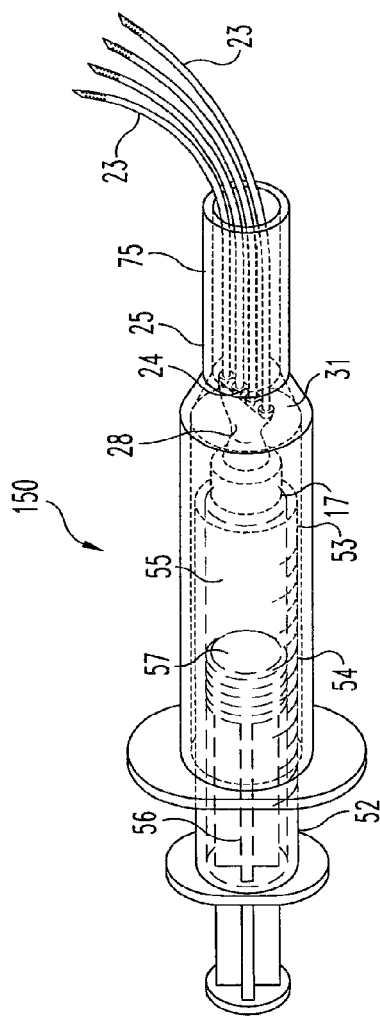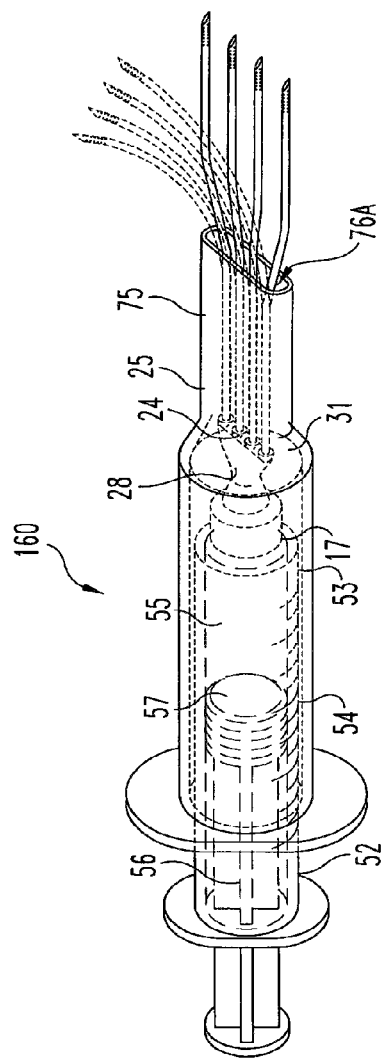
Fig. 13
Fig. 14

DEVICES AND METHODS FOR DELIVERING MEDICAL AGENTS

CROSS-REFERENCE TO RELATED APPLICATIONS

This application is a continuation of U.S. patent application Ser. No. 11/118,125 filed Apr. 29, 2005, the entirety of which is incorporated by reference.

BACKGROUND

The present invention relates generally to devices useful for delivering medical agents to patient tissues, and in one particular aspect to medical delivery devices such as needles that provide improvements in the diffuse or regional delivery of medical agents through a volume of patient tissue.

As further background, many needle devices in current use deliver a single stream of medical agent, and either provide a focused delivery of the agent, or require frequent repositioning to distribute the agent through a volume of tissue. Repeated positioning of a device can cause discomfort to the patient and can lead to extended tissue damage. Additionally, current devices and methods for delivering medical agents can cause localized pressure as the agent is delivered, making delivery of additional amounts of agent more difficult and potentially causing other patient-related complications.

In view of this background, needs remain for improved or alternative medical agent delivery devices and methods, including for example those that facilitate regional delivery of the agent and/or reduce complications which may arise due to pressure increases in the immediate and/or surrounding tissues. The present invention provides embodiments addressed to these and other needs.

SUMMARY

The present invention provides medical delivery devices, such as needles, that can be used to effectively distribute a medical agent to multiple sites within a tissue volume without requiring the device to be repositioned, including for example to distribute the medical agent within the nucleus pulposus tissue of a spinal disc. In certain embodiments, medical delivery devices of the invention are also configured to simultaneously remove fluid from the tissue volume into which a medical agent is being delivered, thus avoiding or otherwise decreasing any pressure build-up and facilitating an effective, uniform delivery of the therapeutic agent. In specific embodiments, methods and devices are adapted for medical agent delivery into nucleus pulposus tissue of a spinal disc. Such deliveries in accordance with the invention provide particular advantage in many respects, since the nuclear tissue of the disc is substantially non-vascularized and thus the native capacity for distribution of the medical agent is limited. As well, in instances where the disc annulus remains substantially intact or has a relatively small opening, a relatively closed volume exists into which the agent is to be delivered thus increasing the potential for pressure build within the disc space and/or undesired expulsion of delivered and/or tissue material back out of the opening.

In one aspect, the present invention thus provides a medical device useful in the regional delivery of a medical agent into tissue of a patient. The medical device includes one or more medical agent supply reservoirs, and a plurality of elongate tissue-penetrating members, such as non-coring needles, each having a fluid channel. Each of the tissue-penetrating members has a plurality of orifices in communication with its fluid channel, for expelling medical agent delivered through the fluid channel. In turn, the fluid channels of the tissue-penetrating members are in fluid communication with the medical agent supply reservoir(s). A mechanism such as a plunger is provided for delivering medical agent from the supply reservoir(s) through the fluid channels and out of the orifices. In certain embodiments, the fluid channels of the tissue-penetrating members are in fluid communication with a medical agent supply reservoir common to all of them, while in other embodiments each fluid channel can communicate selectively with a separate supply reservoir. The needles or other tissue-penetrating members can have any of a number of configurations, or combinations thereof, including curved or straight configurations when relaxed (unconstrained).

In another embodiment, the invention provides a medical needle device useful for regional delivery of a medical agent. The needle device includes one or more medical agent supply reservoirs, and one or more elongate needles having a sidewall, a fluid channel extending longitudinally therethrough, and a non-coring, tissue-penetrating needle tip. The fluid channel of each elongate needle communicates with a plurality of sidewall orifices in the needle through which medical agent delivered through the fluid channel is expelled. The fluid channel of each elongate needle is, in turn, in fluid communication with the one or more medical agent supply reservoirs. A mechanism is provided for delivering amounts of medical agent from the supply reservoir(s) through the fluid channel(s) and out of the sidewall orifices.

The present invention also provides a method of delivering a medical agent to the interior disc space of a spinal disc. The method includes the steps of introducing amounts of the medical agent to the interior disc space, and removing amounts of tissue material from the disc space so as to decrease (including eliminate) pressurization of the interior disc space caused by introduction of the medical agent. As examples, removal of amounts of fluid and/or other disc tissue material can be conducted simultaneously with the delivery of amounts of medical agents, intermittently between deliveries of amounts of the medical agent, or combinations thereof. In advantageous forms, such methods of the invention can be conducted by (a) providing a medical agent delivery device including:
   one or more elongate tissue-penetrating members, such as needles, for penetrating through the disc annulus and into the interior disc space;
   a first orifice on the one or more tissue-penetrating members;
   a first fluid path extending from the first orifice;
   a delivery mechanism for delivering a medical agent fluidly coupled to the first fluid path;
   a second orifice on the one or more tissue penetrating members;
   a second fluid path extends from the second orifice; and
   a withdrawal mechanism for withdrawing material from tissue of the patient is fluidly coupled to the second fluid path;

(b) manipulating the delivery device to position the first orifice and the second orifice in the interior disc space; and (c) operating the delivery mechanism and the withdrawal mechanism so as to deliver medical agent to and remove material from the interior disc space.

In other embodiments, methods of the invention include providing a medical agent delivery device including a plurality of exit orifices in fluid communication with a supply of the medical agent. The delivery device is manipulated to position the plurality of exit orifices in non-vascularized disc nucleus tissue within the interior disc space. The medical agent is delivered from the plurality of exit orifices to a plurality of locations within the non-vascularized disc nucleus tissue.

In other aspects, the invention provides medical agent delivery devices configured to deliver a medical agent to patient tissue via a first fluid path and remove material from the patient tissue via a second fluid path. In certain embodiments, the medical agent delivery devices include one or more elongate tissue-penetrating members, such as needles, for penetrating into a tissue region of the patient. A first orifice is provided on the one or more tissue-penetrating members, with a first fluid path extending from the first orifice. A delivery mechanism for delivering a medical agent is fluidly coupled to the first fluid path. A second orifice is also provided on the one or more tissue penetrating members, and a second fluid path extends from the second orifice. A withdrawal mechanism for withdrawing material from tissue of the patient is fluidly coupled to the second fluid path.

In another embodiment, a medical device is provided that is useful for regional delivery of a medical agent. The device includes a medical agent supply reservoir, and a plurality of elongate tissue-penetrating members each having a fluid channel, a tissue-penetrating tip, and at least one orifice for expelling medical agent. The elongate tissue-penetrating members extend in a substantially planar array, with the fluid channels of the elongate members in fluid communication with the medical agent supply reservoir. A mechanism is provided for forcing medical agent from the supply reservoir through the fluid channels and out of the orifices. In certain embodiments, the elongate tissue-penetrating members are each substantially straight when in a relaxed condition to provide a desired medical agent distribution pattern. In other embodiments, the elongate tissue-penetrating members are each curved when relaxed to provide the desired distribution pattern. Combinations of curved and straight penetrating members can also be used.

In another embodiment, the invention provides a medical device useful for regional delivery of a medical agent. The device includes a medical agent supply reservoir and a plurality of elongate tissue-penetrating members each having a fluid channel, at least one delivery orifice in fluid communication with the fluid channel, and a tissue-penetrating tip. The fluid channels of said elongate members are in fluid communication with the medical agent supply reservoir. The device further includes a retraction sleeve having a plurality of internal cannulas, wherein each of the cannulas is configured to slidably receive one of the elongate tissue-penetrating members. The device also has a mechanism for forcing medical agent from the supply reservoir through the fluid channels and out of the delivery orifices. In certain forms, the retraction sleeve has generally straight internal cannulas. In other forms, at least one deflectable tissue-penetrating member is included among the plurality of tissue-penetrating members, and a corresponding internal cannula of the retraction sleeve is configured deflect the at least one deflectable tissue-penetrating member. In advantageous embodiments, a plurality of deflectable tissue penetrating members can be provided, representing either some or all of the total number of tissue-penetrating members on the device. The retraction sleeve can then include internal cannulas corresponding to and configured to deflect each of the deflectable tissue penetrating members. Deflections in these and other embodiments of the invention can, for example, be from a straight to a curved configuration, or vice versa.

Additional embodiments of the invention and related features and advantages will be apparent from the descriptions herein.

BRIEF DESCRIPTION OF THE DRAWINGS

FIG. 1A is an exploded view of one embodiment of a syringe needle assembly according to the present invention.

FIG. 1B is a side elevation view of the syringe needle assembly of FIG. 1A.

FIG. 1C is a side elevation partial cross-section view of the syringe needle tip of FIGS. 1A and 1B.

FIG. 2A is an exploded view of an embodiment of an alternative syringe needle assembly provided according to the present invention.

FIG. 2B is a side elevation view of the syringe needle assembly of FIG. 2A.

FIG. 2C is a side elevational partial cross-section view of the syringe needle tip of FIGS. 2A and 2B.

FIG. 3A is an exploded view of an embodiment of an alternative syringe needle assembly having a manifold and a plurality of needles.

FIG. 3B is a side elevation view of the syringe needle assembly of FIG. 3A.

FIG. 3D is fragmentary view depicting the distal tip region of the needle assembly shown in FIG. 3A.

FIG. 8 is a side elevation view of the syringe needle assembly of FIG. 2 in use to simultaneously deliver and remove fluid material into and from an interior spinal disc space.

FIG. 9 is a side elevation view of the syringe needle assembly of FIG. 5G in use to deliver fluid material into interior spinal disc space.

FIG. 13 illustrates another medical delivery device of the present invention.

FIG. 14 illustrates another medical delivery device of the present invention.

DETAILED DESCRIPTION

Figure 3C:
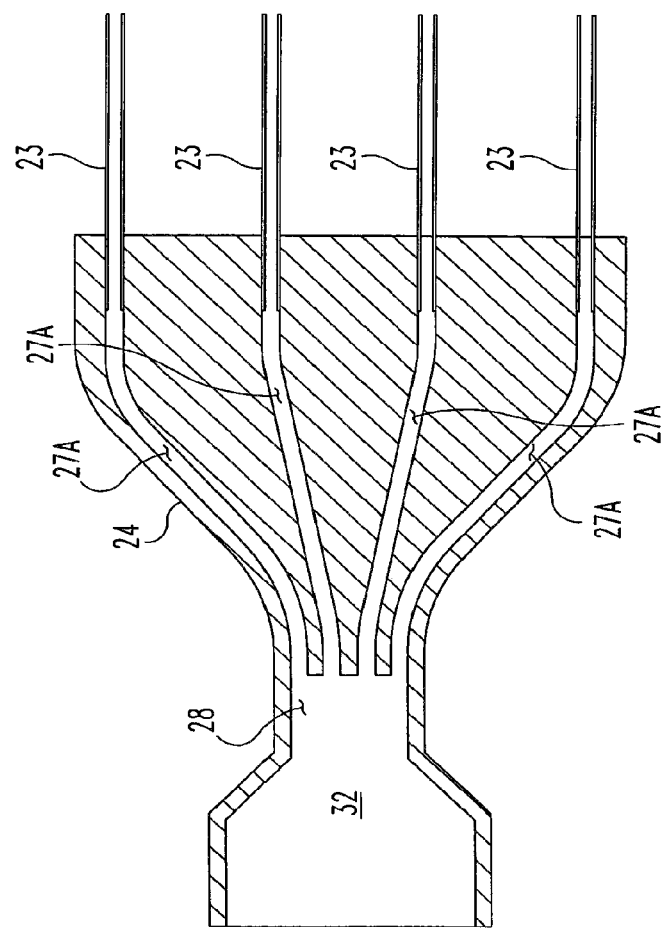
FIG. 3C is a partial cross-sectional view depicting the manifold element and proximal needle region of the syringe needle assembly of FIG. 3A showing internal flow paths.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As disclosed above, the present invention provides methods, medical devices, and components of medical devices useful for delivering one or more medical agents into patient tissues, including in certain specific embodiments into the nucleus of a spinal disc. Certain methods and devices of the invention desirably achieve a regional, rather than single pinpoint, delivery of the medical agent. In alternative forms, methods and devices of the invention capitalize upon the removal of fluid and/or other volume-occupying tissue material to minimize or eliminate pressure buildup upon the delivery of medical substances into the tissue region.

With reference now to FIGS. 1A, 1B and 1C, shown is one embodiment of a medical delivery device of the invention that generally includes a needle 1, in certain embodiments a spinal needle configured for penetration through a disc annulus and into nucleus pulposus tissue, and a syringe 50. Needle 1 comprises an elongated member 10 formed of a biocompatible material and has a proximal end 11, a distal region 12, and a plurality of orifices or apertures 13 at its distal region. The elongated member 10 additionally has an inner surface 14 (FIG. 1C) defining a lumen 15 or fluid channel within and along its length. The distal end of elongated member 10 has a penetrating (desirably non-coring) tip 16 to assist penetration into a spinal disc or other patient tissue and ensure the delivery of a medical agent through apertures 13. The proximal end of elongated member 10 has a connector 17 for engaging a distal end of syringe 50. Syringe 50 has a housing 54 having a proximal end 52, a distal end 53 and forming a cavity or internal chamber 55 to provide a supply reservoir for the medical agent. Syringe 50 additionally has a syringe plunger 56 equipped with a plunger head 57 and a connector 51 for attaching to connector 17 of spinal needle 1. With reference particularly to FIG. 1B, the syringe 50 and spinal needle 1 of FIG. 1A are engaged through luer-lock connectors 17 and 51 causing cavity 55, lumen 15 and apertures 13 to be in fluid communication. It will be understood, however, that other mechanisms or means for connecting the needle 1 and syringe 50 can be used and are contemplated as being within broader aspects of the present invention.

With reference to FIGS. 2A, 2B and 2C, another medical delivery device of the invention is illustrated that includes a needle 2 and syringe 50. Like needle 1 (FIGS. 1A-1C), spinal needle 2 comprises an elongated tissue-penetrating member formed of a biocompatible material and has a proximal end 11, a distal region 12, and a plurality of orifices or apertures 13 and 36 in the distal region. Orifice 21 and connector 19 are located at the proximal end 11 of elongated member 10. Connector 19 has a lumen 35 and is positioned over orifice 21 causing orifice 21 and lumen 35 to be in communication. The proximal end of elongated member 10 additionally has a connector 17 for engaging a distal end of syringe 50. The elongated member's distal region 12 has a closed penetrating tip 22. Inner member 46, a wall-like structure in contact with the interior surface 14, partitions the interior of elongated member 10 and in combination with inner surface 14, forms first channel 15 and second channel 20 (see e.g. FIG. 2C). Inner member 46 is positioned within elongated member 10 to cause lumen 35, orifice 21, channel 20, and apertures 36 to be in fluid communication and provide a pathway independent of channel 15 for withdrawal of fluid from a spinal disc or other patient tissue. Inner member 46 is similarly positioned to provide for fluid communication between channel 15 and apertures 13. Syringe 50 has a housing 54 having a proximal end 52, a distal end 53 and a cavity or chamber 55. Syringe 50 additionally has a syringe plunger 56 equipped with a plunger head 57 and a connector 51 for attaching to connector 17 of needle 2. With reference particularly to FIG. 2B, the syringe 50 and needle 2 of FIG. 2A are engaged through luer-lock connectors 17 and 51 causing cavity 55, lumen 15 and apertures 13 to be in fluid communication and providing a route for the delivery of a therapeutic agent from syringe 50 through apertures 13. As before, other arrangements for associating the needle and syringe 50 can be used.

With reference to FIGS. 3A, 3B and 3C and 3D, another embodiment of a medical device is illustrated that generally includes a needle assembly 3 and a syringe 50. Needle assembly 3 includes a plurality of elongate tissue penetrating members (four needles in the illustrated embodiment) formed of a biocompatible material. In particular, at the proximal end 11, needle assembly 3 has a manifold component 24 and at its distal region 12, a plurality of elongated penetrating members 23 in a generally planar arrangement. Each elongated member 23 has a proximal end 25, a distal region 26 and a plurality of sidewall apertures 13 in its distal region. Elongated members 23 and the manifold piece 24 additionally have inner surfaces 14 and 28 (see e.g. FIG. 3C) defining elongate member lumens 27 and manifold cavity 32. Manifold component 24 also defines a plurality of lumens 27A which receive the proximal ends of elongate members 23 and communicate with their lumens 27. The distal end of elongated member 23 has a closed penetrating tip 22 to assist penetration into a spinal disc upon the application of pressure and allow the delivery of a therapeutic agent through sidewall apertures 13 which in the illustrated embodiment are distributed radially around elongated members 23. The proximal end of manifold piece 24 has a connector 17 for engaging a distal end of syringe 50. Manifold cavity 32 is in fluid communication with lumens 27 and apertures 13. Syringe 50 is as described with regard to FIG. 1. With reference particularly to FIG. 3B, the syringe 50 and spinal needle 3 of FIG. 3A are engaged through luer-lock connectors 17 and 51 causing syringe cavity 55, manifold cavity 32, lumen 27 and apertures 13 to be in fluid communication.

Figure 4A:
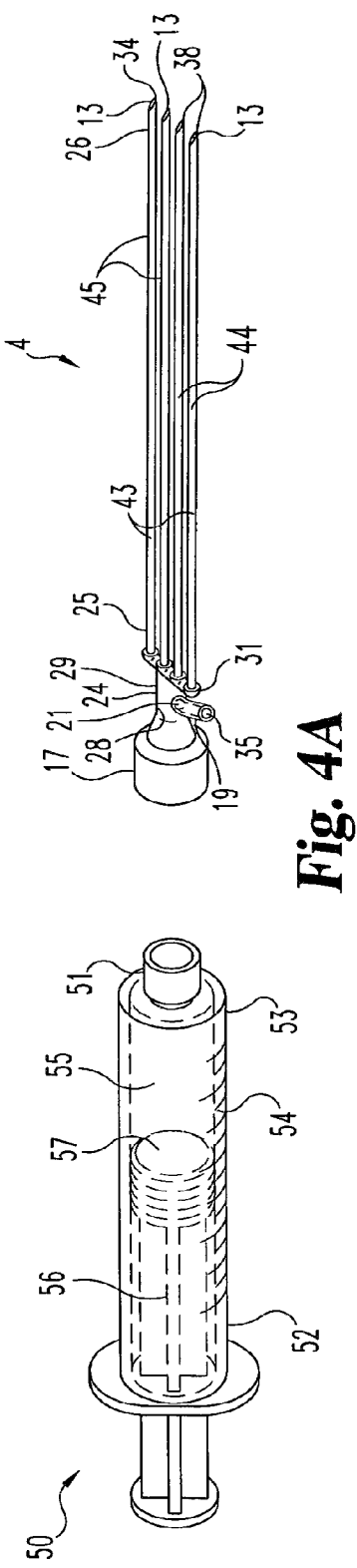
FIG. 4A is an exploded view of an embodiment of an alternative syringe needle assembly having elongate needle members devoted to fluid delivery and withdrawal.
Figure 4C:
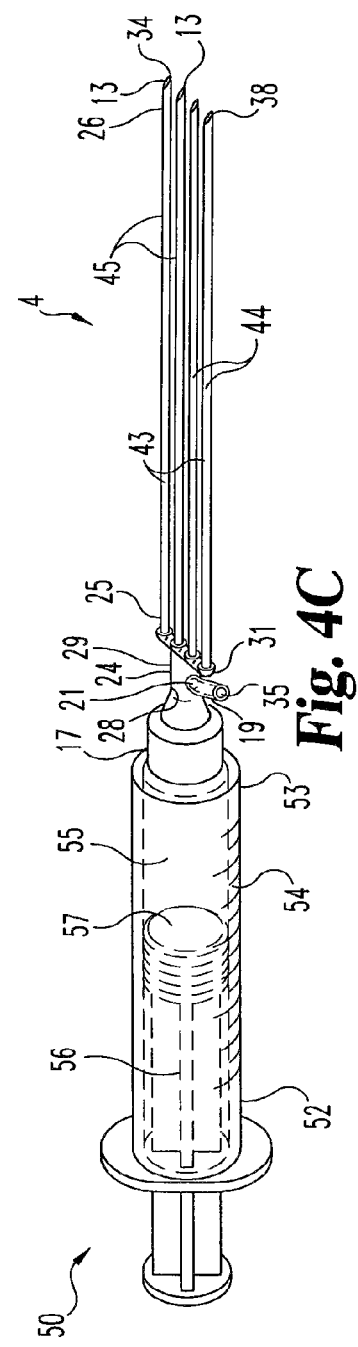
FIG. 4C is a side elevation view of the syringe needle assembly of FIG. 4A.
Figure 4B:
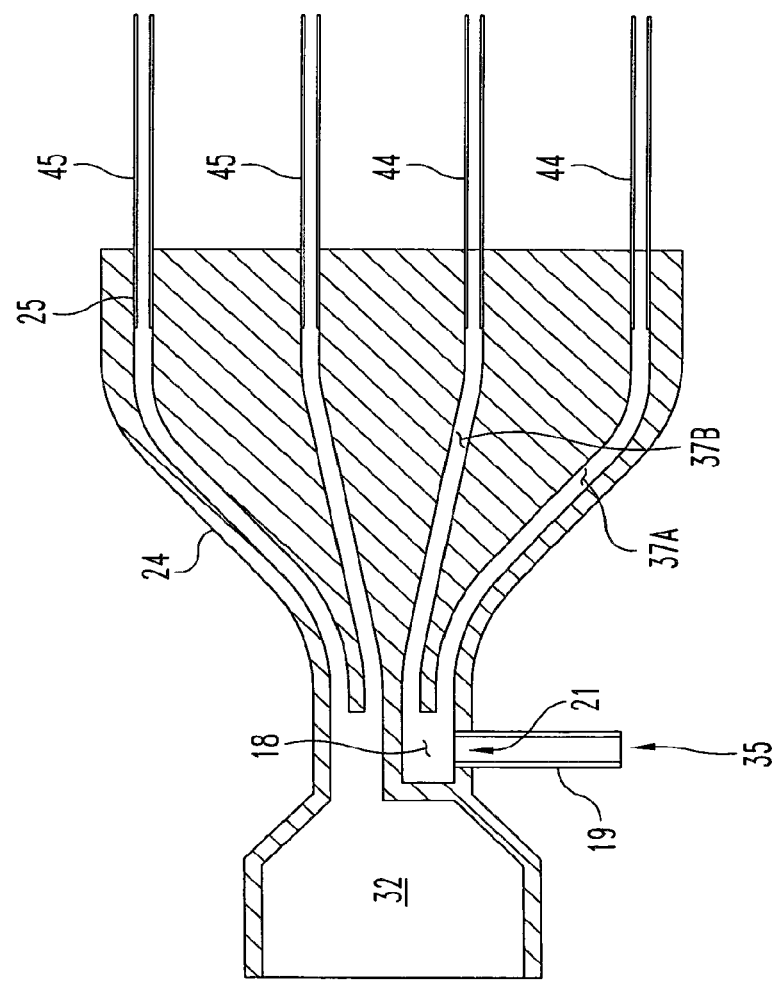
FIG. 4B is a sectional view of the manifold component of the syringe needle assembly of FIG. 4A illustrating separate internal fluid paths for fluid delivery and withdrawal.

With reference to FIGS. 4A, 4B and 4C, another embodiment of an inventive medical delivery device is illustrated that includes a needle assembly 4 and syringe 50. This device is similar to that depicted in FIGS. 3A and 3B, except having separate internal pathways for delivery of medical agent and removal of tissue (e.g. fluid) material. In particular, needle assembly 4 includes a manifold piece 24 and a plurality of elongated tissue penetrating members 44 and 45. Needle assembly 4 has inner walls providing an independent internal pathway 18 for withdrawing or otherwise allowing passage of fluid and/or other material from a spinal disc or other tissue region in conjunction with delivering a therapeutic or other medical agent. Manifold element 24 has a connector 19 positioned on the manifold's outer surface about aperture 21. Connector 19 provides lumen 35 in communication with orifice 21, with channels 37A and 37B of internal pathway 18 and with lumens 42 within elongated members 44 (FIG. 4B). Elongated members 44 and 45 have a proximal end 25, a distal end 26, a penetrating tip 34 at the distal end 26, and a plurality of apertures 13 and 38. Syringe 50 is as described with regard to FIG. 1. With reference to FIG. 4C, the syringe 50 and needle assembly 4 of FIG. 4A are engaged through luer-lock connectors 17 and 51 causing syringe cavity 55, manifold cavity 32, lumens 43 within delivery members 45 and apertures 13 to be in fluid communication. Thus, plunger 56 can be actuated to deliver medical agent from syringe cavity 55 into manifold cavity 32, through lumens 43 and out of apertures 13. At the same time, tissue fluid or other material can be withdrawn from the tissue volume to receive the medical agent through internal pathway 18 including apertures 38 in elongate members 44, through internal lumens 42, and out through lumen 35. In this regard, the withdrawal of fluid can be active, in the sense that a negative pressure can be applied to pathway 18 through lumen 35 (e.g. using a syringe) to withdraw tissue material, or can be passive in the sense that pressure created in the receiving tissue volume due to the delivery of medical agent can force tissue fluid or other material out through pathway 18.

Figure 5A:
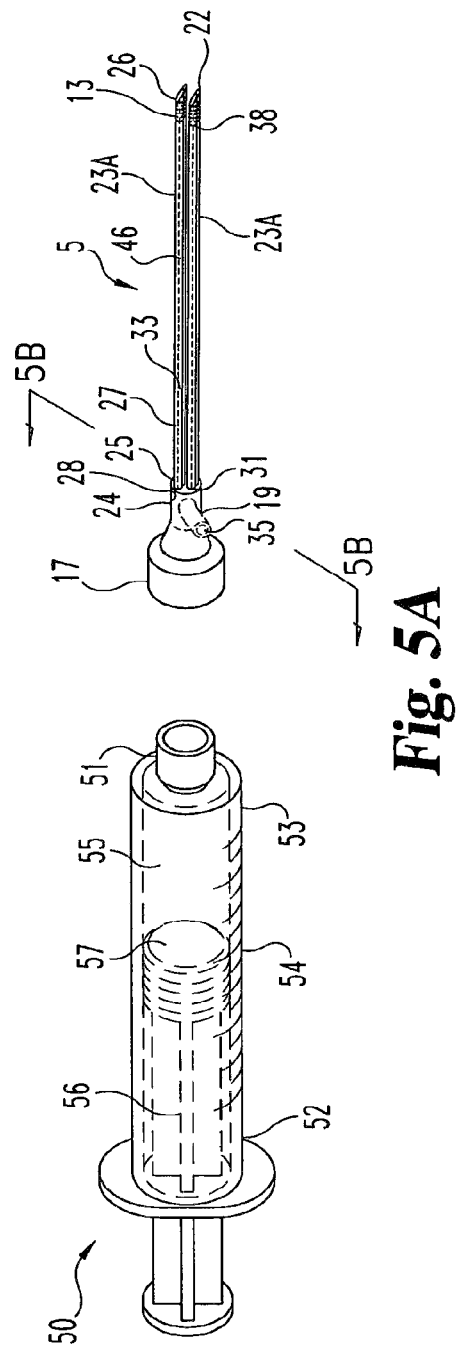
FIG. 5A is an exploded view of an alternative syringe needle assembly having a manifold and having elongated members devoted to fluid delivery and withdrawal.
Figure 5B:
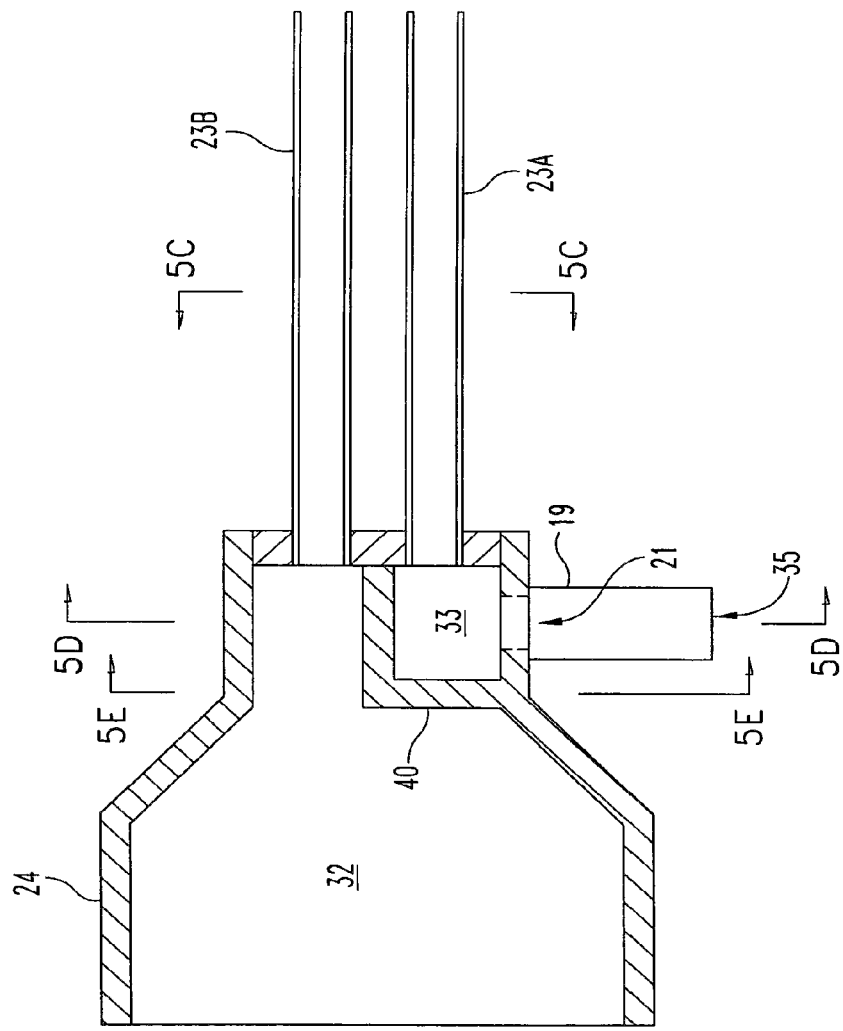
FIG. 5B is a partial sectional view of the needle assembly of FIG. 5A illustrating separate internal fluid paths for fluid delivery and withdrawal.
Figure 5C:
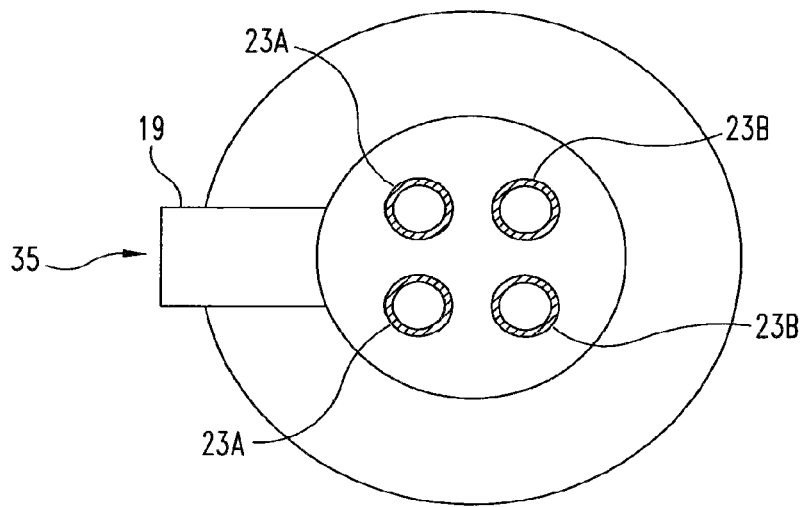
FIG. 5C is a cross-sectional view taken along line 5C-5C of FIG. 5B and viewed in the direction of the arrows.
Figure 5D:
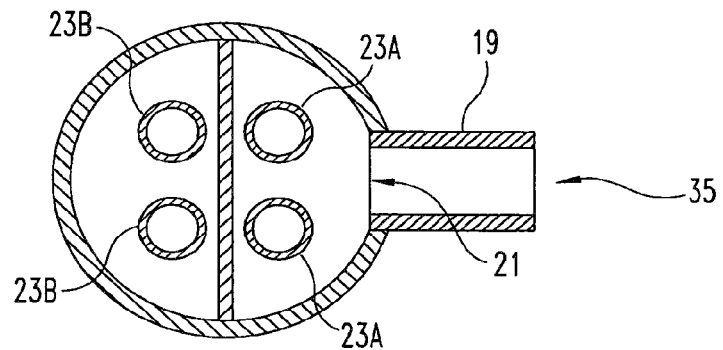
FIG. 5D is a cross-sectional view taken along line 5D-5D of FIG. 5B and viewed in the direction of the arrows.
Figure 5E:
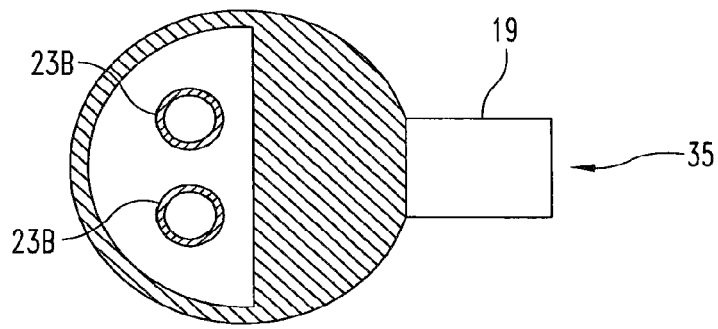
FIG. 5E is a cross-sectional view taken along line 5E-5E of FIG. 5B and viewed in the direction of the arrows.
Figure 5F:
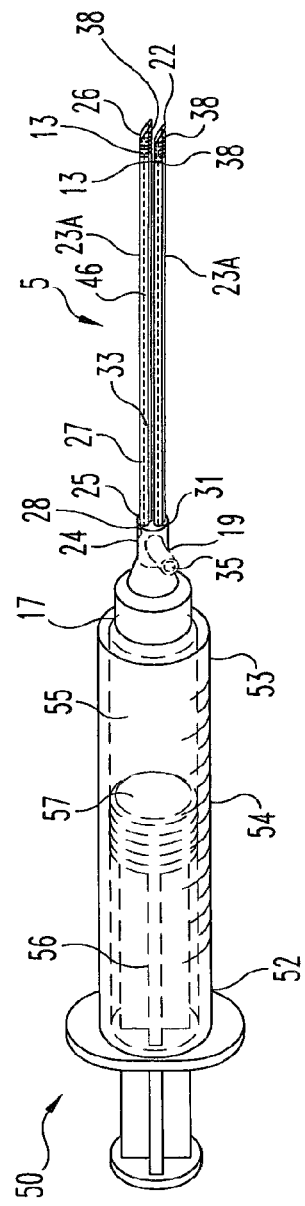
FIG. 5F is a side elevation view of the syringe needle assembly of FIG. 5A.

With reference to FIGS. 5A through 5F, another embodiment of an inventive medical delivery device is illustrated that includes a needle assembly 5 and syringe 50. Needle assembly 5 includes a manifold element 24 and a plurality of elongated tissue penetrating members 23A and 23B constructed from a biocompatible material. Needle assembly 5 is configured to allow for the simultaneous deliver and withdrawal of materials from a spinal disc or other tissue. Withdrawal is achieved through apertures 38 of withdrawing elongate members 23A coupled to withdrawal pathway including channel 33, orifice 21, and lumen 35 of connector 19. The delivery of a medical agent is achieved through apertures 13 of delivery elongate members 23B by way of manifold cavity 32. FIG. 5B is a sectional view of the spinal needle of FIG. 5A illustrating the needle's internal structure. An internal pathway is provided within the elongated members 23A and manifold 24 causing apertures 38, channel 33, orifice 21 and lumen 35 within connector 19 to be in fluid communication. A separate internal pathway is provided causing apertures 13, lumen 27, and manifold cavity 32 to be in fluid communication. With reference to FIG. 5C, a cross-section of the elongated members 23A and 23B taken along line 5C-5C of FIG. 5B and viewed in the direction of the arrows is provided illustrating the position of the elongate members. With reference to FIG. 5D, a cross-section of the proximal end of manifold element 24 taken along line 5D-5D of FIG. 5B is provided illustrating manifold cavity 32 for receiving and transferring medical agent(s) delivered to the patient, and channel 33 for directing material withdrawn from the patient through orifice 21 and lumen 35. With reference to FIG. 5E, a cross section of manifold element 24 at internal wall 40 is provided illustrating the cavity 32 in fluid communication with the connector opening of manifold element 24 for medical agent delivery and internal wall 40 interrupting fluid communication with the connector opening of manifold element 24 and thereby establishing a separate chamber or channel (33, FIG. 5B) for fluid withdrawal. With reference to FIG. 5F, the syringe 50 and needle assembly 5 of FIGS. 5A-5E, are engaged through luer-lock connectors 17 and 51 causing syringe cavity 55, manifold cavity 32, lumens 27 and apertures 13 to be in fluid communication.

Figure 5G:
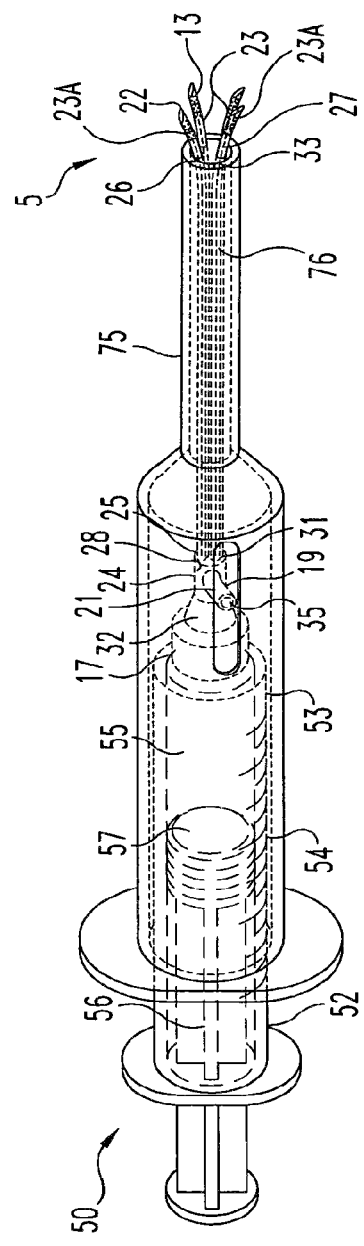
FIG. 5G is a side elevation view of the syringe needle assembly of FIG. 5F in combination with a retaining sleeve with dedicated internal lumens that receive and deflect individual needles to provide a desired injection pattern.

With reference to FIG. 5G, shown is an inventive medical delivery device including the assembly of FIG. 5G engaged with a cannulated retraction sleeve member 75 having a plurality of cannulas 76 having curved end portions to deflect elongated members 23A and 23B to provide a desired injection pattern. In this regard, elongate members 23A and 23B for this embodiment can be constructed of a biocompatible material that is resiliently flexible or deflectable from a relaxed (e.g. straight) configuration, whereby the curved cannulas 76 direct the elongated members to the desired injection pattern when the tips of elongated members 23A and 23B are advanced through and out of the curved cannulas 76, and the elongated members return substantially to their relaxed (e.g. straight) condition when withdrawn back into the cannulas 76 beyond their curved end portions. In other embodiments, the cannulas 76 are straight, and the elongate members have a curved configuration when relaxed but are deflectable to a straight configuration for travel through the cannulas 76. Upon exiting cannulas 76 the elongate members assume their curved configuration to provide the desired delivery pattern. As well, combinations of curved lumens and curved elongate members can be used to achieve a desired delivery pattern. Still further, in alternative embodiments, either some or all of the plurality of elongate members can be of a deflectable nature, and each deflectable elongate member can have a corresponding, dedicated cannula in the cannulated member configured to provide deflection to the desired delivery pattern.

As shown in FIG. 5G, cannulated member 75 can be configured to slide overtop syringe 50 and can include handle or grip elements for facilitating manipulation in proximal and distal directions relative to syringe 50. As well, cannulated member 75 can include windows or cutouts for any syringe components that need or are desired to exit the side of cannulated member 75 (e.g. as in the connector 19 of syringe 50).

Figure 6:
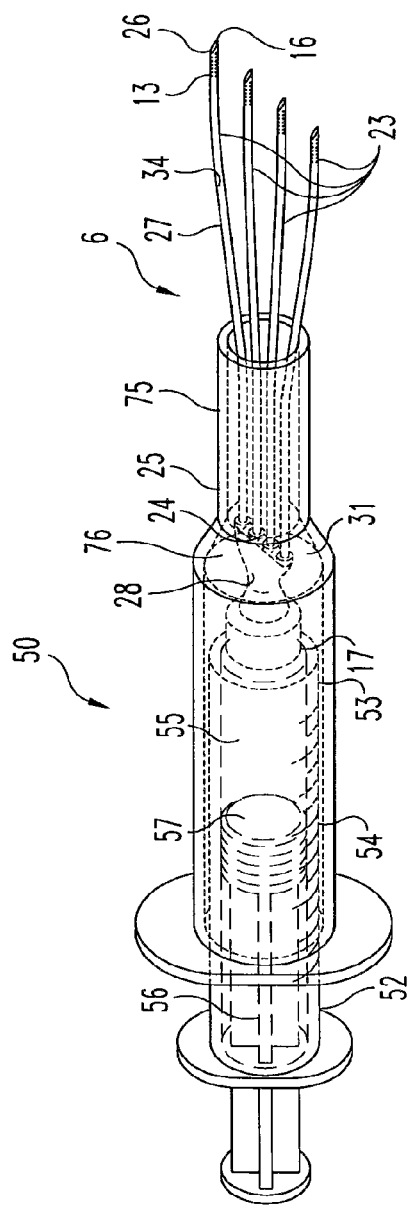
FIG. 6 is a side elevation view of an embodiment of a syringe needle assembly having the distal ends of the elongated members partially expelled from a retaining sleeve having a single internal lumen.

With reference to FIG. 6, an embodiment of an inventive medical device is illustrated that includes a needle assembly 6 and syringe 50. Needle assembly 6 is similar in construction to that shown in FIGS. 3A, 3B and 3C, and has elongated penetrating members 23 constructed of flexible biocompatible material having shape memory properties capable of being constrained within sleeve or cannulated member 75 having a single lumen 76 and assuming an original configuration when expelled from lumen 76. In the embodiment shown, the outermost members 23 have curved portions in their unconstrained (relaxed) condition thereby providing a generally wider, planer delivery configuration.

Figure 7:
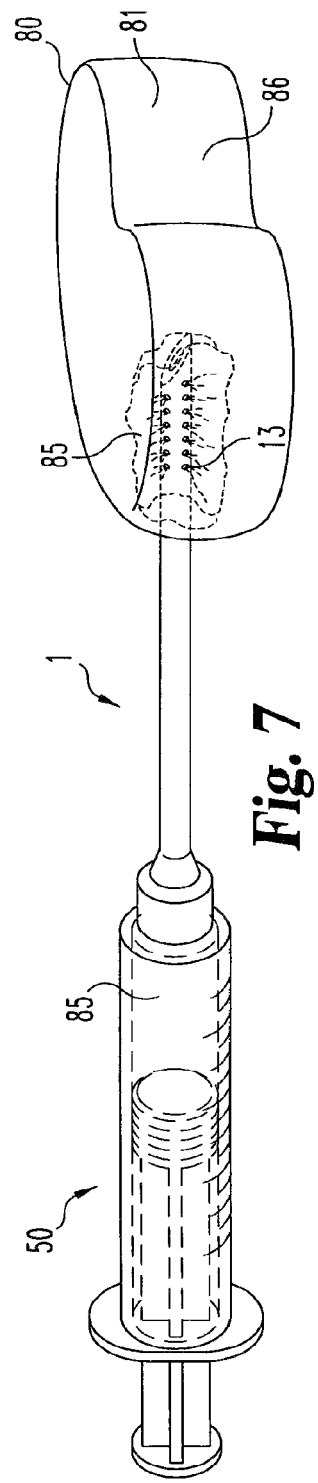
FIG. 7 is a side elevation view of the syringe needle assembly of FIG. 1 in use to deliver a medical agent into an interior spinal disc space.

FIG. 7 illustrates the medical delivery device of FIG. 1B in use. In particular, medical agent 85 is being delivered through the plurality of apertures 13 into the nucleus 81 of identified spinal disc 80 to which access has been provided, for example minimally invasive access using the syringe needle assembly potentially in combination with a tubular introducer sleeve.) Although syringe 50 attached to spinal needle 1 is fitted with a plunger 56 and plunger head 57, a syringe having a screw drive mechanism, a ratcheting mechanism, a trigger, or another delivery mechanism for forcing or otherwise moving the medical agent through the system can be utilized with needle assembly 1 and other needle assembly embodiments of the invention.

FIG. 8 shows the medical delivery device of FIG. 2B in use. After providing access to disc 80 (e.g. minimally invasive access as discussed above) a medical agent 85 is shown being delivered with needle assembly 2 through apertures 13 into the nucleus 81 of spinal disc 80 simultaneously with the withdrawal of material (e.g. tissue fluid) 86 through apertures 38, for example using a separate syringe device 100 coupled to connector 19. It will be understood that syringe device 100 could be replaced with a simple container that can collect fluid at ambient pressure in situations wherein the pressure generated in the disc or other tissue bed is sufficient to drive fluid and/or other tissue material through the withdrawal fluid path (i.e. assisted withdrawal with reduced pressure or other active mechanisms will not necessarily be required in all situations). Connector 19 can be adapted to be fitted with a flexible tubing or fitted with a special connector such as a luer-lock fitting to assist in creating a suitable pathway into syringe device 100 or another collection device.

FIG. 9 illustrates the syringe needle assembly of FIG. 5G in use. After providing minimally invasive or other access to disc 80, a medical agent 85 is shown being delivered with needle assembly 5 through apertures 13 into the nucleus 81 of spinal disc 80 simultaneously with the withdrawal of fluid 86 through apertures 38 and delivered into syringe 100 through connector 19. The elongated members 23 are engaged in cannulated member 75 having a plurality of lumens 76 which direct the elongated members 23 according to a desired delivery pattern. To achieve delivery, the end of cannulated member 75 can be docked or positioned against the disc annulus while the elongated penetrating members 23 are fully received in sleeve 75. The syringe-needle assembly (50 and 5) can then be advanced into sleeve 75 to drive the penetrating members 23 through their respective curved lumens, out the end of sleeve 75, through the disc annulus, and into the nucleus 81. The sleeve 75 with its curved lumens allows penetration of the disc annulus in a defined, relatively small region, but directs the members 23 to a desired, differing pattern, such as a more spaced pattern, a directional pattern deflected from the longitudinal axis of the sleeve 75 (e.g. to the right, the left, up or down), a radial pattern, etc. After delivery of the medical agent is complete; the syringe needle assembly can be pulled back through cannulated member 75 to withdraw members back into their respective, dedicated lumens, and the overall device removed from the operational field.

Figure 10:
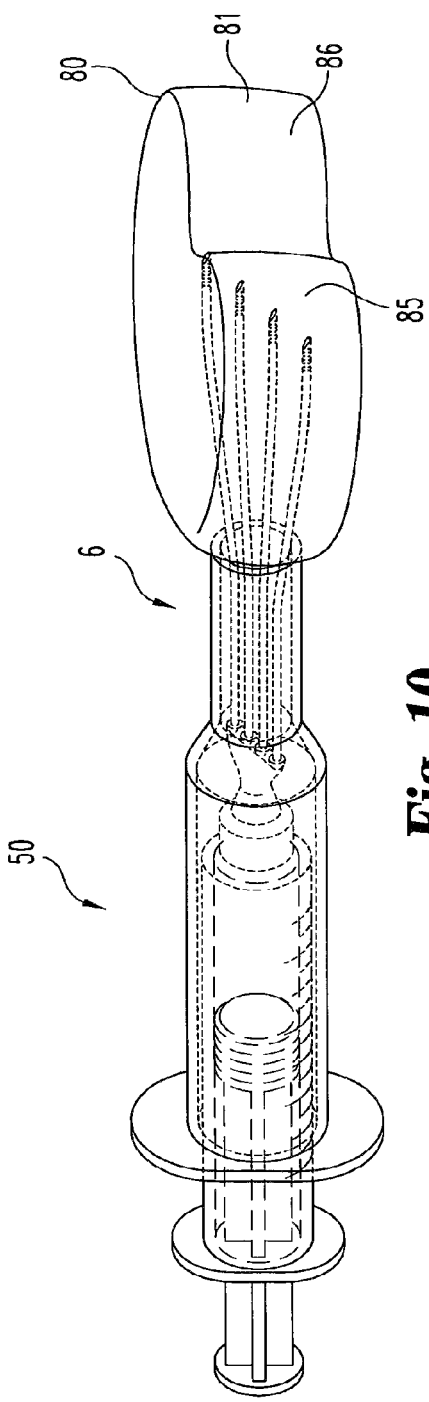
FIG. 10 is a side elevation view of the syringe needle assembly of FIG. 6 in use to deliver fluid material into interior spinal disc space.

FIG. 10 shows the medical delivery device of FIG. 6 in use. After providing access to disc 80, a medical agent 85 is shown being delivered with needle assembly 6 through apertures 13 into the nucleus 81 of spinal disc 80. The elongated members 23, constructed from a biocompatible material having shape memory properties are engaged in sleeve 75 having a single lumen 76. When fully engaged within sleeve 75, the elongated members 23 are constrained together and as they are expelled during insertion into spinal disc 80 they separate, regaining their original, wider conformation to deliver the therapeutic agent according to a predetermined delivery pattern. Again, to achieve delivery, the sleeve 75 can be positioned against the disc annulus with the elongate members 23 fully received therein, whereafter the members can be ejected from the sleeve 75 to penetrate the annulus and enter into the nucleus pulposus tissue within. The medical agent can then be delivered from the elongate members 23 by actuation of the syringe plunger, whereafter the members 23 can be retracted back into sleeve 75, and the delivery device removed from the operational field.

Figure 11:
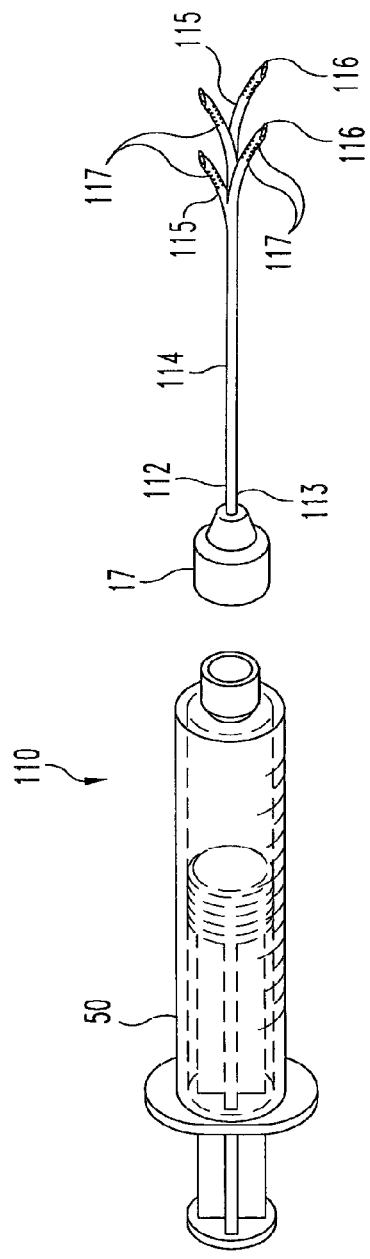
FIG. 11 is a side elevation view of another syringe needle assembly of the present invention.

With reference to FIG. 11, shown is another medical delivery device 110 of the invention. Device 110 includes a syringe 50 as previously described, and a needle assembly 112. Needle assembly 112 includes a connector 17 for fluid connection to syringe 50, and a branching elongate needle 113. Branching needle 113 includes a straight portion 114 having an internal lumen that is common to and feeds a plurality of branching needle portions 115 which extend arcuately and radially away from the longitudinal axis of the straight portion 114. Each branching portion 115 includes a tissue penetrating tip 116, and a plurality of sidewall sidewall 117 for delivery of a medical agent. Tissue penetrating tips 116 can be open, but are preferably closed to facilitate advantageous flow of medical agent out of sidewall orifices 117. In advantageous embodiments, branching elongate needle 114 is constructed of a resilient material such that branching portions 115 can be constrained to a smaller overall profile for delivery into a spinal disc or other tissue region, potentially within single lumen sleeve members (e.g. 75) as described hereinabove, which sleeve members themselves may incorporate tissue penetrating tips for facilitating penetration to a desired tissue level for launch of the needles (e.g. 114) received therein.

Figure 12A:
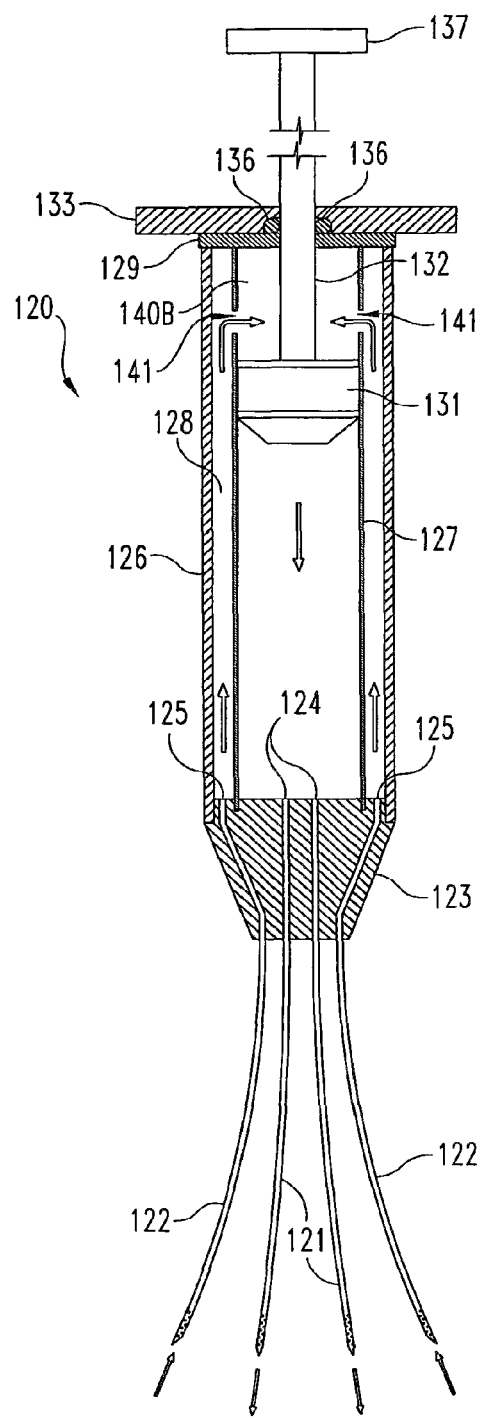
FIG. 12A is a midline cross-sectional view of a syringe needle assembly of the invention configured to inject and remove material simultaneously upon the actuation of a single plunger.
Figure 12B:
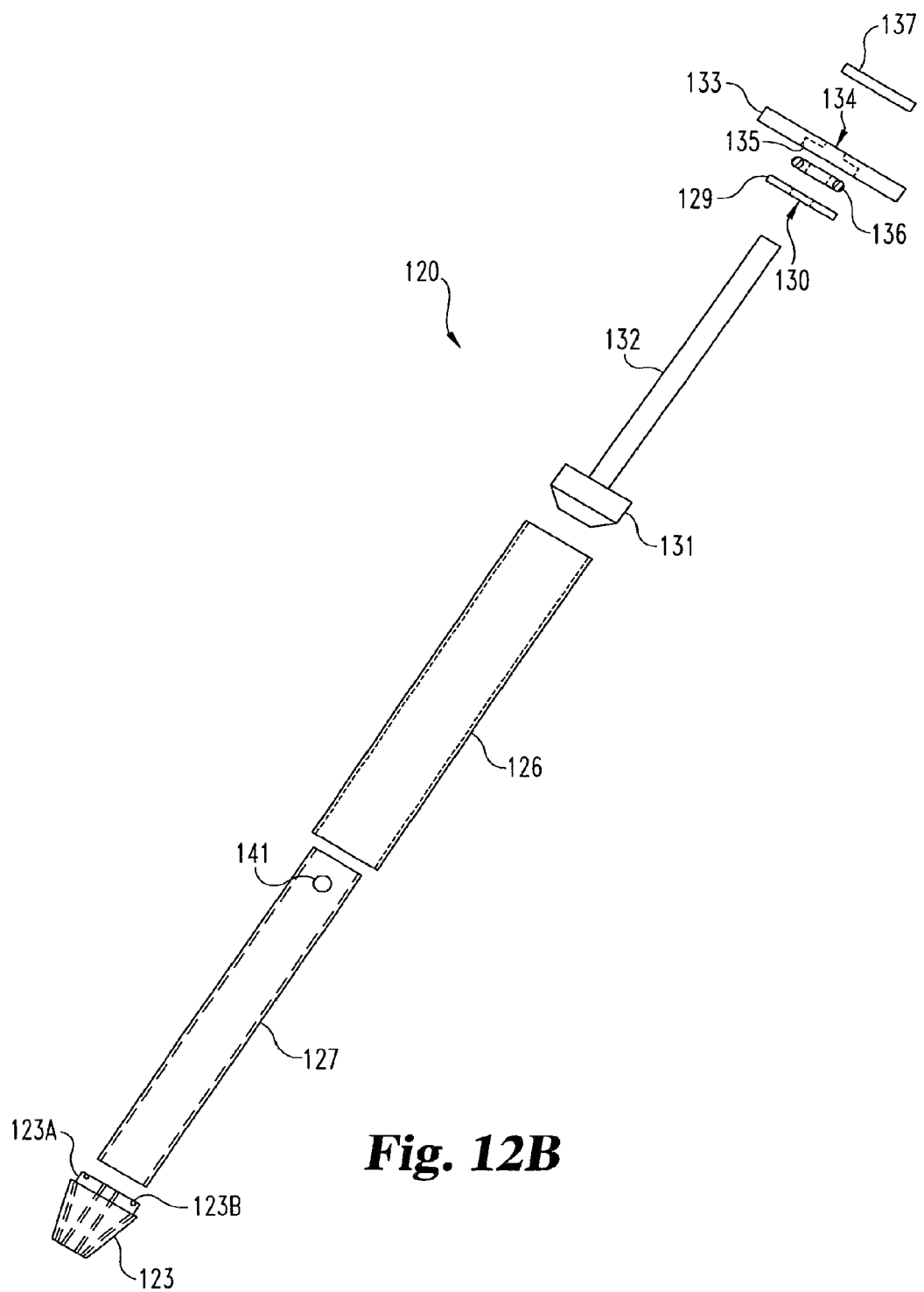
FIG. 12B is an exploded view of syringe of the syringe needle assembly of FIG. 12A.

With reference to FIGS. 12A and 12B, an further medical agent delivery device of the present invention will be described. The illustrated device 120 is configured to simultaneously deliver and withdraw material from patient tissue upon actuation of a single syringe plunger. Generally, in the illustrated device 120, medical agent forward of an advancing plunger head will be expelled through one or more first fluid paths, and material such as fluid from within tissue of the patient will be withdrawn though one or more second fluid paths coupled to and activated by a negative pressure zone generated rearward of the advancing plunger head (see, generally, arrows in FIG. 12A illustrating material flow directions). In this manner, a simple operation can be performed to both deliver and withdraw material to and from patient tissue, and the delivered and withdrawn material will be of substantially the same volume since the volumetric displacement forward and rearward of the advancing plunger head will be similar.

Turning now specifically to the features of the drawings, delivery device 120 includes a plurality of needles 121 and 122 which, as shown, can include a curved configuration in a relaxed condition. Straight, deflectable or non-deflectable needles can also be used within the invention, as discussed above. Needles 121 and 122 have their distal ends received within a distal cap piece 123. Distal cap piece 123 defines a plurality of internal lumens 124 and 125 corresponding to and communicating with internal lumens of needles 121 and 122. Device 120 has a barrel portion defined by an outer cylindrical member 126 and an inner cylindrical member 127, which define a generally annular chamber 128 between them. The distal end of the outer cylindrical member 126 is sealingly received around shoulder portion 123A of distal cap member 123, while the distal end of inner cylindrical member 127 is sealingly received within an annular notch 123B defined within distal cap member 123.

At the proximal end of device 120, proximal cap member 129 having a central opening 130 is sealed against the proximal ends of outer and inner cylindrical members 126 and 127. The plunger apparatus includes plunger head 131 received within and cooperating with the internal walls of inner cylindrical member 127. Plunger arm 132 is connected to plunger head 131 and extends through central opening 130 in proximal cap 129. In the illustrated device 120, plunger arm 132 is either a hollow or solid cylinder, although other shapes can also be used within the invention. A proximal grip plate 133 is secured to the outer surface of proximal cap 129. Grip plate 133 includes a central opening 134 generally corresponding in size to the central opening 130 of proximal cap 129, and is grooved partially through its thickness about the opening to create an annular shoulder 135, which in turn creates an internal volume when the grip plate 133 is secured to the proximal cap 129. A sealing element such as an "O"-ring 136 is received within such internal volume, and cooperates to substantially maintain a pressure seal against plunger arm 132 as it is advanced into and withdrawn from the barrel of device 120. A push-pull handle element 137 is provided at the end of plunger arm 132 to facilitate manually advancing and withdrawing the plunger apparatus in and out of the device 120.

That portion of inner chamber 140A (defined by the internal volume of inner cylindrical member 127) forward of the plunger head 131 fluidly communicates with lumens 124 for delivery of a medical agent from forward chamber 140B through and out of delivery needles 121. Annular chamber 128 fluidly communicates with that portion of inner chamber 140B rearward of plunger head 131 through one or more openings 141 defined in inner cylindrical member 127. Annular chamber 128, in turn, fluidly communicates with peripheral lumens 125 defined in distal cap 123, which communicate with internal lumens of withdrawal needles 122. It will be understood that needles 121 and 122 can include a single opening at their distal end, and/or can include one or a plurality of sidewall openings 142 as in other needles disclosed hereinabove.

In operation, chamber portion 140A forward of plunger head 131 can be filled with a medical agent at manufacture, or just prior to delivery. The latter may be achieved, for example, by advancing the plunger head 131 to its forward-most position within inner cylindrical member 127, positioning the distal ends of delivery needles 121 into a volume of the medical agent, and drawing the plunger back up the inner cylindrical member 127 (but desirably stopping short of openings 141). Thereafter, the distal ends of needles 121 and 122 can be advanced into disc nucleus or other tissue for delivery, and plunger head 131 advanced distally within inner cylindrical member 127. In this manner, the medical agent will be delivered from forward chamber portion 140A through lumens 124 and out of sidewall openings 142 of delivery needles 121. At the same time, a negative pressure zone will be created rearward of the plunger 131 within rearward chamber portion 140B, and this negative pressure will be communicated through openings 141 into annular chamber 128, through lumens 125 and ultimately to sidewall openings 142 in withdrawal needles 122. Fluid or other tissue will thereby be withdrawn under pressure from the nucleus pulposus or other tissue, will fill into annular chamber 128, and if sufficient in volume will spill through holes 141 and into rearward chamber portion 140B occurring behind the now-advanced position of plunger head 131. After this, in one mode of use, needles 121 and 122 can be withdrawn from the patient tissue while leaving the plunger head in its advanced position after delivery of the medical agent.

It will be understood that a variety of other configurations can be used while achieving a simultaneous delivery and withdrawal of material as effectuated by device 120 of FIGS. 12A and 12B. For example, an inverse operation can be provided, wherein a medical agent to be delivered is originally loaded rearward of plunger head 131 in an advanced position and within annular chamber 128, and the plunger head 131 withdrawn proximally to force the agent out of needles 121 while simultaneously withdrawing material from needles 122. As well, separate plungers could be provided for separate, discrete chambers for withdrawal of material and delivery of material. In one mode, a first plunger could be advanced in a first chamber to deliver an agent through a first needle or needles of the assembly, while a second plunger is withdrawn through a second chamber to withdraw material from a second needle of the assembly. These and still other adaptations can be used within the ambit of the present invention.

In addition or as an alternative to relieving pressure created by delivered medical agent to tissue volumes, the withdrawal (including simultaneous and/or intermittent withdrawal) of patient fluid from adjacent tissue regions can potentially facilitate the creation of flow or diffusion gradients that assist in spreading or regionalizing the delivered agent. Thus, in certain instances, it will be desired to have withdrawal openings somewhat spaced from delivery openings on medical delivery devices of the invention. This spacing will also help to prevent or minimize withdrawal of amounts of the delivered agent when that is undesired. Such spacing may be achieved by having multiple needles with openings spaced from one another as in certain embodiments disclosed herein, and/or by having openings spaced from one another on a single needle having a bifurcated lumen, wherein one side of the bifurcation communicates with one or more delivery openings and the other communicates with one or more withdrawal openings. Spacing of delivery and withdrawal openings may be achieved for example by radial spacing and/or by longitudinal spacing along a single needle body.

Referring now to FIG. 13, shown is another medical delivery device 150 of the present invention. Device 150 is similar to the device depicted in FIGS. 6 and 10, except elongate members 23 have a relaxed condition in which they each curve to one direction away from the longitudinal axis of device 150 and provide a generally planar, laterally-facing ejection pattern. In this fashion, device 150 can be advanced to position sleeve 75 against the annulus fibrosus of a spinal disc, and elongate members 23 advanced out of sleeve, through the annulus fibrosus (or an opening already therein), whereafter upon further advancement they assume their original laterally-facing configuration for delivery of agent to one side of the interior disc space. The members 23 can thereafter be withdrawn back into sleeve 75, and either the sleeve/needle/syringe assembly rotated 180 degrees, or the needle/syringe assembly rotated within the sleeve 180 degrees. Advancement of the members 23 out of sleeve member 75 again thereafter enables delivery of amounts of the medical agent to the other side of the interior space of the disc.

FIG. 14 depicts still another medical delivery device 160 of the present invention. Device 160 can have syringe-needle assemblies similar to those depicted in FIGS. 6 and 13. Device 160, however, includes a retraction sleeve having a modified, more flattened distal region and an elongate opening 76A such as an elongate ovate opening. Elongate opening 76A beneficially contributes to assuring that needles 23 remain in a substantially planar array. In this regard, needles 23 can be generally straight and provide a planar array, can include needles that flare but return to extend generally parallel to their original longitudinal axis (as shown in FIG. 15), can curve laterally to one side (shown in phantom in FIG. 15) or both sides, or any combination of these or other desired configurations.

The medical agent delivered to the patient using methods and devices of the present invention can be, for example, therapeutic or diagnostic. Diagnostic agents include, for example, imaging agents such as x-ray contrast agents, magnetic resonance imaging (MRI) agents, and the like. Therapeutic agents may include, for example, cells, including disc nucleus cells and/or adult or embryonic stem cells, drugs, anti-inflammatory agents, tissue growth factors, anesthetics, antibiotics, MMP inhibitors, extracellular matrix components, keratin-family proteins, platelet-rich plasma, bone marrow, morphogenic proteins including bone morphogenic proteins such as BMP-2 or BMP-7, nucleic acid constructs such as expression vectors including nucleic acid molecules encoding morphogenic proteins such as those mentioned above or LIM mineralization protein (LMP), and a wide variety of other known medical agents. Such medical agents can be delivered in certain embodiments in controlled release fashion, for example by the injection of suspensions of controlled release particles such as controlled release microspheres which are deposited within the recipient tissue (e.g. disc nucleus pulposus tissue) for sustained release of the medical agent.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. It should be understood that while the use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. A method of delivering a medical agent to an interior disc space of a spinal disc, the method comprising:
   providing a medical agent delivery device comprising one or more elongate tissue-penetrating members for penetrating into a tissue region of the patient;
   a first orifice located on said one or more tissue-penetrating members;
   a first fluid path from said first orifice;
   a delivery mechanism for delivering a medical agent, said delivery mechanism fluidly coupled to the first fluid path, said delivery mechanism includes a delivery plunger operatively associated with a medical agent supply chamber and adapted to deliver medical agent from the supply chamber through said first fluid path;
   a second orifice on said one or more tissue penetrating members;
   a second fluid path from said second orifice; and
   a withdrawal mechanism for withdrawing material from tissue of the patient, said withdrawal mechanism fluidly coupled to said second fluid path, said withdrawal mechanism includes a withdrawal plunger operatively associated with at least one tissue material receiving chamber and adapted to withdraw tissue material through said second fluid path; and
   wherein the first fluid path and the second fluid path are independent of each other;
   said medical agent supply chamber is provided by a barrel;
   said plunger and barrel are configured so that said plunger is traversable through the barrel so as to force medical agent forward of the plunger through said first fluid path and also create a reduced pressure zone rearward of the plunger in the barrel; and
   said second fluid path is coupled to said reduced pressure zone such that traversal of the plunger through the barrel simultaneously delivers medical agent to the tissue region and withdraws tissue material from the tissue region;
   positioning the medical agent delivery device so as to insert said first orifice and second orifices into the interior space of the spinal disc;
   delivering a medical agent from said first orifice located on said one or more tissue-penetrating members to a disc nucleus tissue within the interior disc space.

2. The method of claim 1, wherein said delivering and withdrawing are conducted intermittently.

3. The method of claim 1, wherein said delivering and withdrawing are conducted simultaneously.

4. The method of claim 1, wherein withdrawing material from the disc nucleus tissue decreases pressurization of the interior space caused by delivering the medical agent.

5. The method of claim 1, wherein said medical agent comprises a therapeutic agent.

6. The method of claim 1, wherein said therapeutic agent comprises a tissue growth factor or a nucleic acid molecule.

7. The method of claim 6, wherein said tissue growth factor is BMP-2 or BMP-7.

8. The method of claim 1, wherein said manipulating and delivering are performed in a minimally invasive procedure.

9. The method of claim 1, further comprising providing a cannulated element, and wherein manipulating the medical agent delivery device so as to position said first orifice and second orifices in the interior space of the spinal disc comprises inserting at least a part of the medical agent delivery device within the cannulated element.

10. The method of claim 1, further comprising manipulating the medical agent delivery device so as to position said first orifice and second orifices in the interior space of the spinal disc to multiple positions within said disc nucleus tissue and depositing medical agent at said multiple positions.

* * * * *